US006975984B2

(12) United States Patent
MacAuslan et al.

(10) Patent No.: US 6,975,984 B2
(45) Date of Patent: Dec. 13, 2005

(54) ELECTROLARYNGEAL SPEECH ENHANCEMENT FOR TELEPHONY

(75) Inventors: Joel M. MacAuslan, Nashua, NH (US); Venkatesh Chari, North Andover, MA (US); Richard Goldhor, Belmont, MA (US); Carol Espy-Wilson, Cambridge, MA (US)

(73) Assignee: Speech Technology and Applied Research Corporation, Bedford, MA (US)

(*) Notice: Subject to any disclaimer, the term of this patent is extended or adjusted under 35 U.S.C. 154(b) by 732 days.

(21) Appl. No.: 09/778,675

(22) Filed: Feb. 7, 2001

(65) Prior Publication Data

US 2001/0033652 A1 Oct. 25, 2001

Related U.S. Application Data

(60) Provisional application No. 60/181,038, filed on Feb. 8, 2000.

(51) Int. Cl.[7] ........................ G10L 11/06; G10L 21/02; A61F 2/20

(52) U.S. Cl. ...................... 704/208; 704/210; 704/226; 704/271; 381/70

(58) Field of Search ................................ 704/208, 210, 704/219, 233, 226, 271; 381/70

(56) References Cited

U.S. PATENT DOCUMENTS

| | | | |
|---|---|---|---|
| 4,495,620 A | 1/1985 | Steele et al. | 370/118 |
| 4,829,574 A | 5/1989 | Dewhurst et al. | 381/41 |
| 5,195,166 A | 3/1993 | Hardwick et al. | 395/2 |
| 5,216,747 A | 6/1993 | Hardwick et al. | 395/2 |

(Continued)

FOREIGN PATENT DOCUMENTS

EP 0 132 216 A1 1/1985

(Continued)

OTHER PUBLICATIONS

"Application of Noise Reduction Techniques for Alaryngeal Speech Enhancement"; Cole et al. TENCON '97. IEEE Region 10 Annual Conference. Speech and Image Technologies for Computing and Telecommunications., vol.: 2, Dec. 2-4, 1997. pp.: 491-494 vol. 2.*

(Continued)

*Primary Examiner*—W. R. Young
*Assistant Examiner*—James S. Wozniak
(74) *Attorney, Agent, or Firm*—Hamilton, Brook, Smith & Reynolds, P.C.

(57) ABSTRACT

A technique for separating an acoustic signal into a voiced (V) component corresponding to an electrolaryngeal source and an unvoiced (U) component corresponding to a turbulence source. The technique can be used to improve the quality of electrolaryngeal speech, and may be adapted for use in a special purpose telephone. A method according to the invention extracts a segment of consecutive values from the original stream of numerical values, and performs a discrete Fourier transform on the this first group of values. Next, a second group of values is extracted from components of the discrete Fourier transform result which correspond to an electrolaryngeal fixed repetition rate, F0, and harmonics thereof. An inverse-Fourier transform is applied to the second group of values, to produce a representation of a segment of the V component. Multiple V component segments are then concatenated to form a V component sample stream. Finally, the U component is determined by subtracting the V component sample stream from the original stream of numerical values.

7 Claims, 5 Drawing Sheets

U.S. PATENT DOCUMENTS

| | | | | |
|---|---|---|---|---|
| 5,226,108 | A | 7/1993 | Hardwick et al. | 395/2 |
| 5,581,656 | A | 12/1996 | Hardwick et al. | 395/2.67 |
| 5,701,390 | A | 12/1997 | Griffin et al. | 395/2.15 |
| 5,715,365 | A | 2/1998 | Griffin et al. | 704/208 |
| 5,729,694 | A * | 3/1998 | Holzrichter et al. | 705/17 |
| 5,787,387 | A | 7/1998 | Aguilar | 704/208 |
| 5,890,111 | A * | 3/1999 | Javkin et al. | 704/226 |
| 6,377,916 | B1 | 4/2002 | Hardwick | 704/208 |

FOREIGN PATENT DOCUMENTS

| | | |
|---|---|---|
| WO | WO 96/02050 | 1/1996 |

OTHER PUBLICATIONS

"Enhancement of Alaryngeal Speech by Adaptive Filtering;" Espy-wilson et al. Spoken Language, 1996. ICSLP 96. Proceedings., Fourth International Conference on, vol.: 2, Oct. 3-6, 1996, pp. 764-767 vol. 2.*

* cited by examiner

ELECTROLARYNGEAL SPEECH ENHANCEMENT FOR TELEPHONY

RELATED APPLICATION

This application claims the benefit of U.S. Provisional Application No. 60/181,038 filed Feb. 8, 2000, the entire teachings of which are incorporated herein by reference.

BACKGROUND OF THE INVENTION

An electrolaryngeal (EL) device provides a means of verbal communication for people who have either undergone a laryngectomy or are otherwise unable to use their larynx (for example, after a tracheotomy). These devices are typically implemented with a vibrating impulse source held against the neck.

Although some of these devices give users a choice of two frequency rates at which they can vibrate, most users find it cumbersome to switch between frequencies, even if a dial is provided for continuous pitch variation. In addition, most users cannot release and restart the device sufficiently quickly to produce the silence that is conventional between words in a spoken phrase.

As a result, the perceived overall quality of their speech is degraded by the presence of the device "buzzing" throughout each phrase. Furthermore, many EL voices have a "mechanical" or "tinny" quality, caused by an absence of low-frequency energy, and sometimes an excess at high frequencies, compared to a natural human voice.

Ordinarily, speakers, both normal and electrolaryngeal, close their mouths during inter-word intervals. This reduces the sound of the EL much during these times; the sound is noticeable merely because it is the only sound that the speaker is producing at the time.

SUMMARY OF THE INVENTION

When speech passes through a processing device, such as a digital signal processor applied to process signals in a special-purpose telephone, lower amplitude samples can be recognized as inter-word intervals and removed. The same processor can also alter the low- and high-frequency components of the EL voice, improving its spectrum to more closely match a natural spectrum.

More particularly, the process recognizes that speech sounds consist of modulation and filtering of two types of sound sources: voicing and air turbulence. The source sound is modified by the mouth and sometimes the nose (for nasal sounds); most users of ELs have had their larynges surgically removed but have nearly normal mouths and noses, resulting in normal modulation and filtering. It is their voice that changes. The larynx, natural or otherwise, supplies voicing; this forms the source sound for vowels, liquids ("r" and "l"), and nasals ("m", "n", and "ng").

Several mechanisms can produced turbulence, which is responsible for the speech sounds known as fricatives, such as the "s" sound, bursts such as the release of the "t" in "top", and the aspiration of "h". A few phonemes such as "z" are voiced fricatives, with both sources contributing. Except for the "h" sound, most EL users can typically produce the various turbulence sources nearly normally.

For processing purposes, one difference between these sources is salient. Voicing, either natural or electrolaryngeal, is nearly periodic, producing a spectrum with almost no energy except at its repetition rate (fundamental frequency),

F0, and the harmonics of F0. Turbulence, in contrast, is non-periodic and produces energy smoothly distributed over a wide range of frequencies.

In a process according to the invention, the speech signal, a stream of acoustic energy, is first split into "voiced" (V) and "unvoiced" (U) components, corresponding respectively to the EL and turbulence sources. The EL provides a stream of pulses at a fixed repetition rate F0 that the user can set, approximately 100 Hz. Because of this F0 stability of an EL (cycle to cycle variations of its inter-pulse period are virtually zero), it is convenient to compute the V part of the stream by a process of:

1. digitizing the acoustic signal at a sufficiently high rate such as 16 kHz, to produce a stream of discrete numerical values;
2. extracting a segment of consecutive values from this stream to produce a first sample list of some fixed length covering a few periods of the EL (500 to 1000 samples is typical for 16 kHz sampling);
3. performing a Fourier transform on the first list;
4. extracting into a second list the components of the transform which correspond to the EL's F0 and harmonics thereof; these may be recognized either by their large amplitudes compared to adjacent frequencies or by their occurrence at integer multiples of some single frequency (which is, in fact, F0—whether or not F0 is known or has been estimated before processing the list);
5. inverse-Fourier transforming the second list, to produce a V list (the V part of the segment); and
6. concatenating the V part of each segment to form a V stream.

The U stream can then be computed by subtracting the V stream's values from the original signal's values.

Observe that the U stream consists almost entirely of turbulent sounds (if any). But because the EL is normally much louder than turbulence, overall, and its energy is concentrated in the fundamental and harmonics that define the V stream, the V stream is dominated by the EL. This holds whether or not small amounts of turbulent sounds occur at the same frequencies and thus appear in V.

Now also consider any short segment (e.g., the same 500–1000 samples as above). Using either the original signal's values or the V values over the segment, it can be characterized as an inter-word segment or not. This characterization may depend on (e.g.) total power in the segment; the presence of broad spectral peaks (from the mouth filtering), especially in the V part; and the characterization of preceding segments. Total power alone is by far the simplest and is adequately discriminating in many cases.

The invention thus preferably also includes a process with the following steps:

7. If desired, linearly filter V to improve its spectrum—for example, to boost its low-frequency energy and/or reduce its high-frequency energy;
8. if the segment is determined to be an inter-word segment, such as by its average power level, set the V values of the segment to zero;
9. add the U values, sample by sample, to the altered V values; and
10. output the result—e.g., through a digital-to-analog converter, to produce a processed acoustic stream.

Notice that, if no spectral change to V is desired, it is sufficient to set the original stream's values to zero in any segment that is determined to be inter-word, and simply output that stream.

Figure 1:
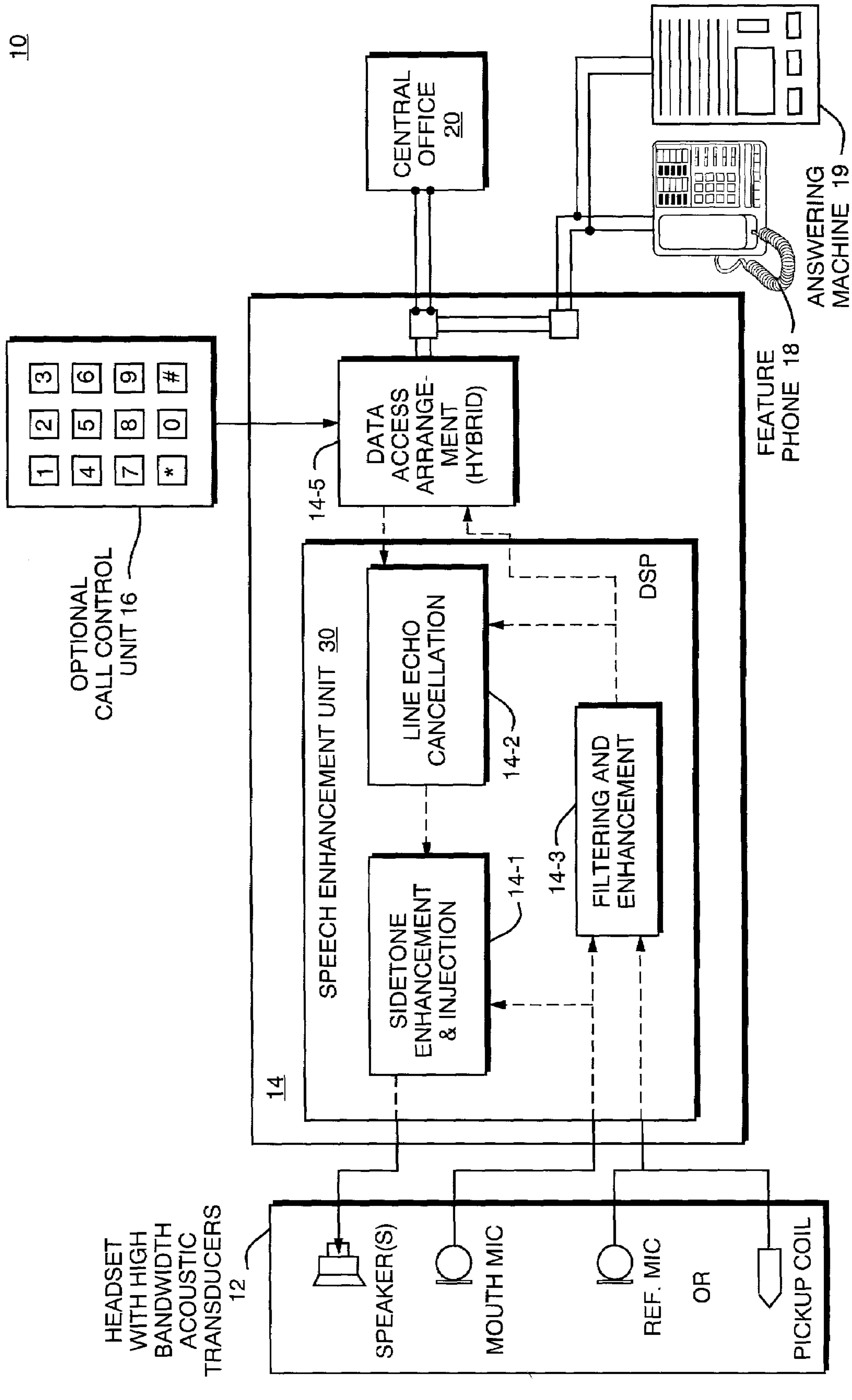
FIG. 1 is a system diagram for one preferred embodiment of the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF A PREFERRED EMBODIMENT

The present invention evolves from the fact that ordinarily speakers, both normal and electrolaryngeal, close their mouths during inter-word intervals. This reduces the sound of the EL device during such times. In particular, speech signals are passed through a processing device such as a special purpose telephone in order to recognize the lower amplitude periods thus permitting their removal from the speech signal. It is also desirable to alter the low and high frequency components of the EL signal to improve its spectrum to match a more natural spectrum more closely.

A system which is capable of performing in this way is shown in FIG. 1. The system 10 consists of a headset with appropriate acoustic transducers including speakers, mouth microphones, reference microphones and/or pickup coils, as shown. The speech enhancement unit 14 consists of a digital signal processor (DSP) 30 performing standard side tone enhancement and injection 14-1, line echo cancellation 14-2, as well as an enhancement process 14-3 in accordance with the invention. A data access arrangement hybrid 14-5 permits signals to be coupled to a telephone central office 20. In addition, signals may be provided to or from a feature telephone 18, answering machine 19, and/or optional call control unit 16.

Figure 2:
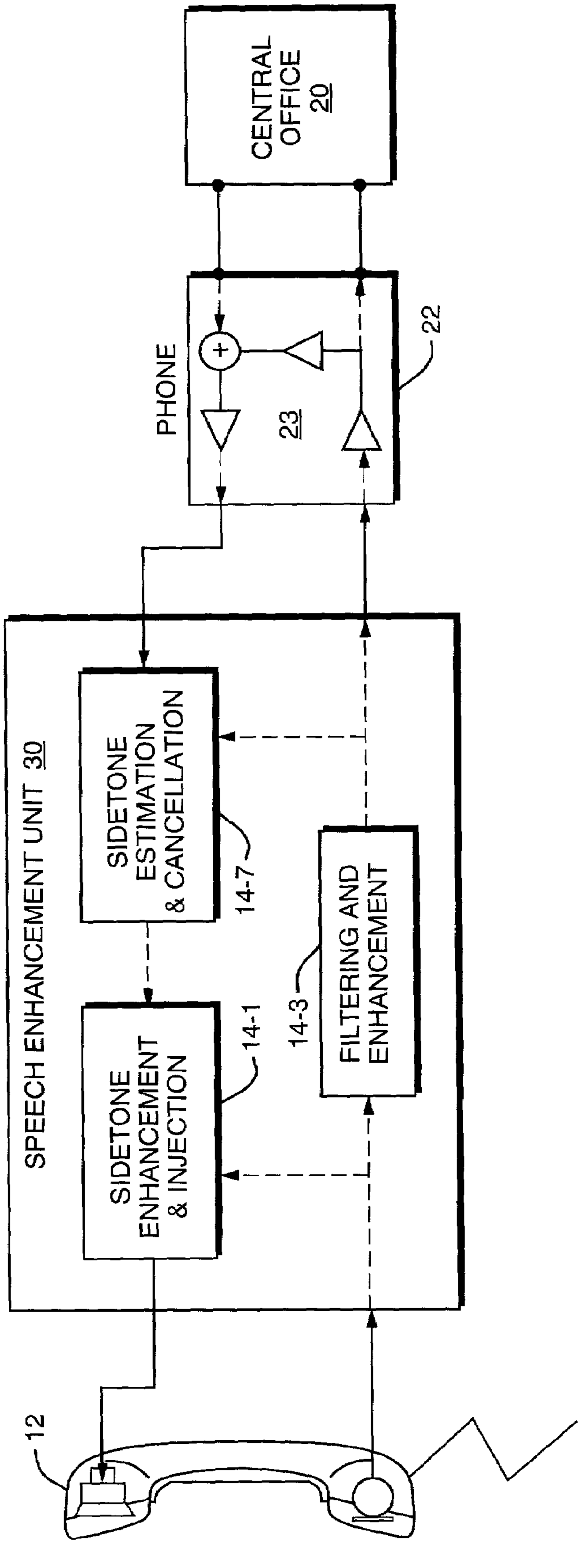
FIG. 2 is a system diagram for an alternate embodiment of the invention.

The invention may also be implemented in simpler device such as shown in FIG. 2. This device consists essentially of a small box containing a digital signal processor 30 that may be connected between the central office 20 and the telephone headset 12 by a two wire cable. The hybrid circuits 23 in the telephone unit 22 can be used to convert DSP signals as necessary to microphone and speaker signals connections as contained within a handset 12. Sidetone path can be estimated and removed by the estimation function 14-7 and enhancement and injection function 14-1. The speech enhancement function 14-3 in accordance with the invention is also performed in the DSP 30 as in the embodiment of FIG. 1.

The implementation of FIG. 2 has the advantage of being a small box which can be connected between the base unit of any ordinary telephone 22 and its associated handset 12. The user can simply carry the box and plug it between the handset and base unit of any phone they happen to locate by means of standard telephone jacks, such as RJ-11 type jacks.

However, the implementation of FIG. 1 has advantages in that the bandwidth of the input signal from the headset microphone may be more precisely controlled. The sensitivity of the speaker and microphone frequency response can also be controlled and processing variations due to characteristics of different telephones 22 can be avoided with the FIG. 1 embodiment.

Figure 3:
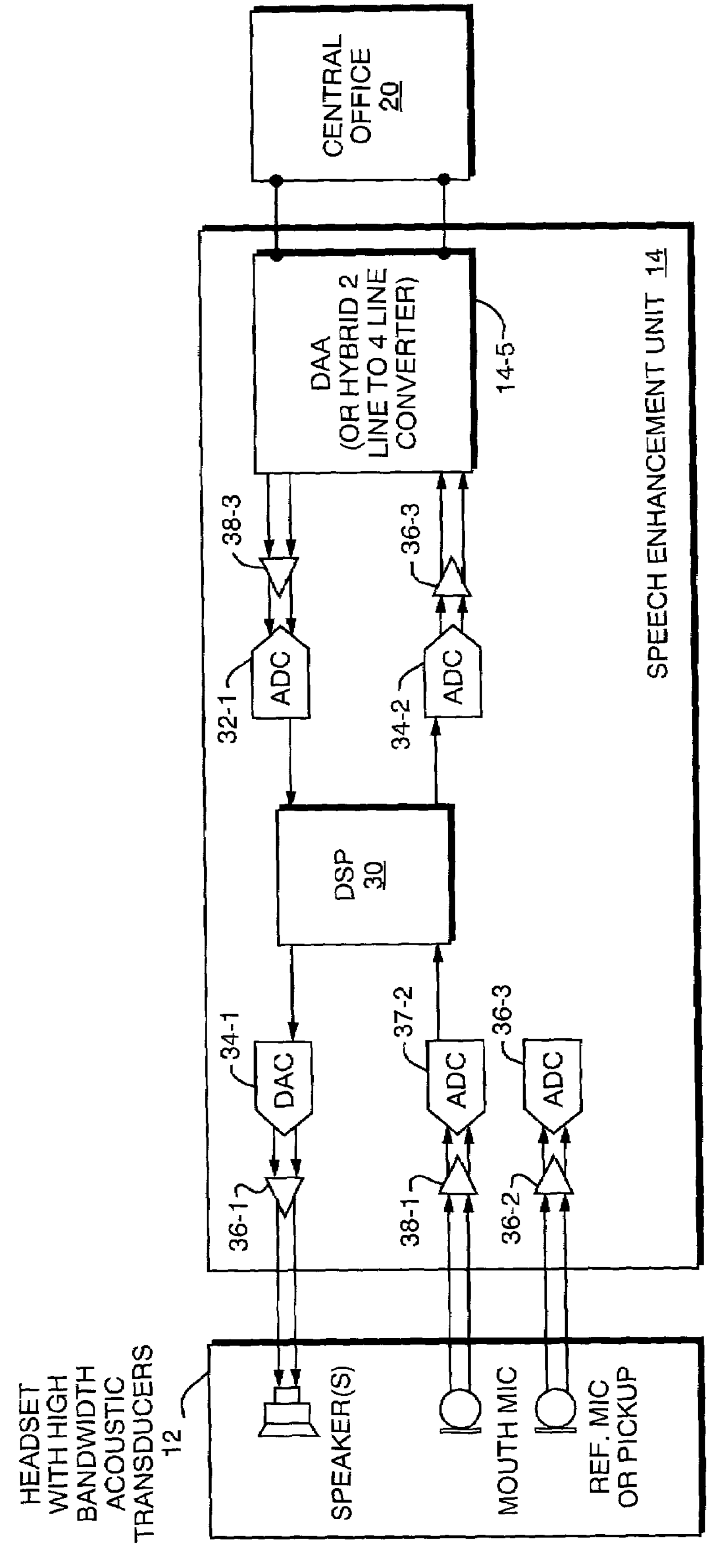
FIG. 3 is a electrical connection diagram for various components of a speech enhancement unit which performs an algorithm according to the invention.

In either event, an electrical system diagram for the speech enhancement function 14-3 is shown in FIG. 3. Essentially, the digital signal processor 30 processes signals received from the central office 20 through either the data access arrangement hybrid 14-5 and/or line converter associated with the phone 22, and provides processed speech signals to the headset 12. In doing so, the DSP 30 makes use of appropriate analog to digital converters 32-1, 32-2, and 32-3, as well as digital to analog converters 34-1 and 34-2. Associated input buffer amplifiers 38-1, 38-2, and 38-3 are used with the analog to digital converters 32. Similarly, output buffer amplifiers 36-1 and 36-2 are utilized with the digital to analog converters 34. Appropriate components for the DSP 30, digital analog converters 34, and data access hybrids 14-5, are known in the art and available from many different vendors.

As mentioned briefly in the introductory portion of this application, normal speakers close their mouths during inter-word intervals. Because it is difficult for electrolaryngeal (EL) device users to mechanically switch the device on and off during short inter-word intervals, their speech is typically degraded by the presence of the device's continuous "buzzing" throughout each spoken phrase. The present invention is an algorithm to be used in the DSP 30 which processes the speech signal to recognize and remove these buzzing sounds from the EL speech. The DSP30 can also alter the low and high frequency components of the EL speech signal to improve its spectrum to more closely match a more natural speaker's voice spectrum.

In the speech enhancement process implemented by the DSP 30, an attempt is made to determine the presence of voiced components (V) and unvoiced components (U) corresponding, respectively, to the electrolaryngeal (EL) and turbulent sources. In particular, turbulent periods are responsible for certain speech sounds, known as fricatives, such as the "s" sound and others, such as the release of the "t" in the word "top", and the aspiration of the sound "h". Other phenomes such as the sound "z" are normally considered to be voiced fricatives, with both sources, the voice source and the turbulent source, contributing to such sounds. Speech sounds thus consist of modulating and filtering of two types of sound sources, voicing and air turbulence. The larynx, natural or artificial, supplies voicing sounds. This forms the source sound for vowels, liquids such as "r" and "l", and nasal sound such as "m" and "ng".

In a first aspect, the invention seeks to implement a process for separating the input speech signal into a stream of acoustic energy, first into the voiced (V) and unvoiced (U) components that correspond respectively to the EL and turbulent sources.

The EL source provides a stream of pulses at a fixed repetition rate, F0, that the user typically sets to a steady rate such as 100 hertz (Hz). Because of the great frequency stability of the electrolaryngeal source (cycle to cycle variations of its inter-pulse period are virtually zero) it is possible to compute the V part of the stream by detecting and then removing this continuous stable source.

Figure 4:
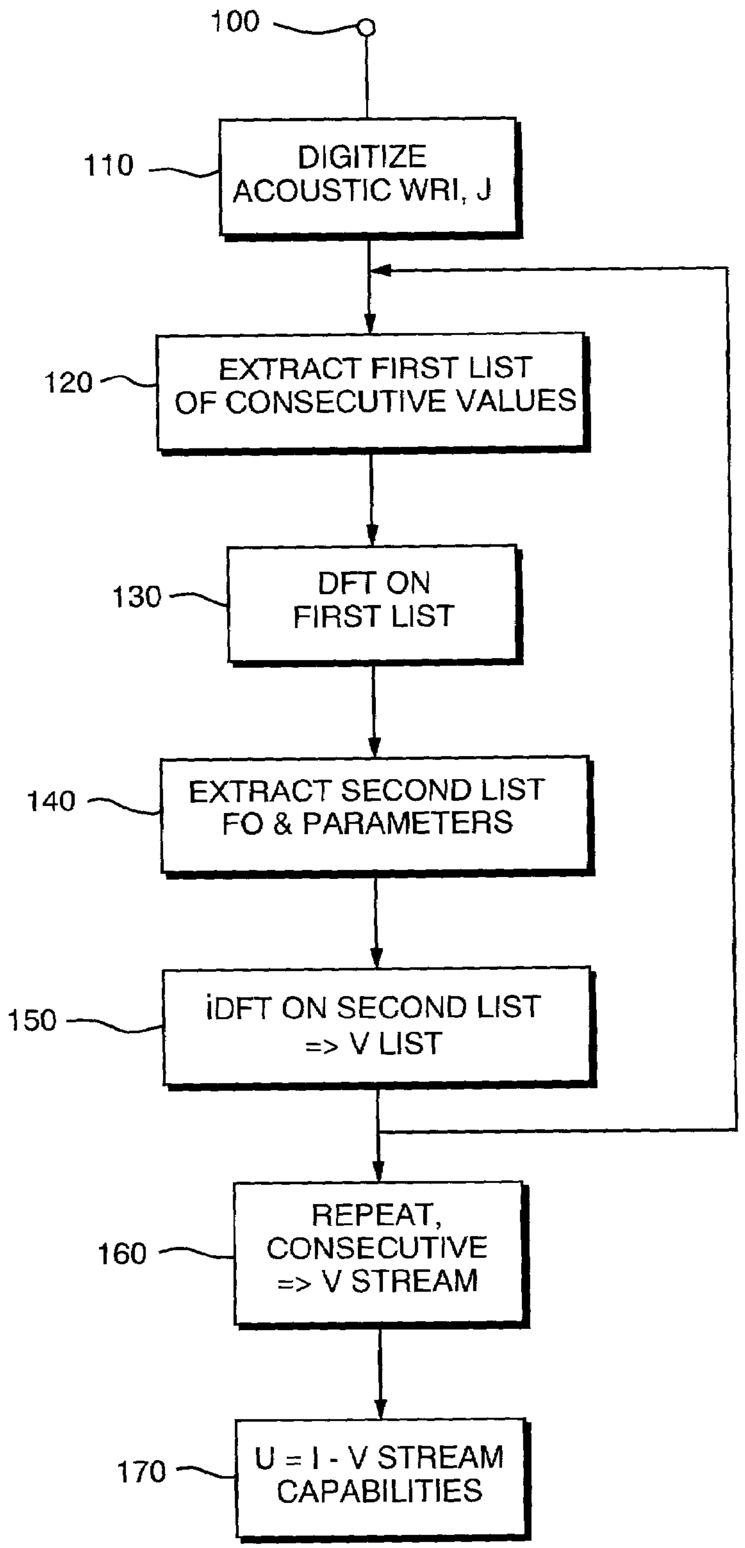
FIG. 4 is a flowchart of the operations performed to determine an unvoiced (U) stream.

A process for performing this function is shown in FIG. 4. From a reference state 100, a state 110 is entered in which an acoustic input signal, I, is digitized. The input acoustic signal I may be digitized at an appropriate rate, such as at 16 kiloHertz (kHz), to produce a stream of discrete numerical values indicating the relative amplitude of the speech signals at discrete points in time.

In a next step 120, a first list of consecutive values is extracted from the input stream I. This first list of values is chosen as a list of some fixed length covering a few periods of the EL source. If, for example, there is 16 kHz sampling and the EL source is a 100 Hz source, a list of from 500≅1000 samples is sufficient.

In a next step 130, a Discrete Fourier Transform (DFT) is performed on this first list. The DFT results are then processed in a next step 140 to extract a second list. The second list corresponds to the components of the DFT output which correspond to the EL sources, F0 frequency and harmonics thereof. These components may be recognized either by their relatively large amplitudes compared to adjacent frequencies, or by their occurrence at integer multiples of some single frequency. This single frequency will in fact be F0, whether or not F0 is known in advance or has been estimated before the list is processed.

In a next step 150, an inverse Discrete Fourier Transform (iDFT) is taken on the second list. This iDFT then provides a time domain version of the voiced (V) part of the segment.

In step 160, the process can then be repeated to provide multiple voiced segments (V) to form a V stream consisting of many such samples.

Once a V stream has been computed, an unvoiced stream (U) can be determined by simply subtracting the voiced stream values from the original input signal (I) values. We note here that the U sample stream consists almost entirely of turbulent sounds, if any. However, because the EL source is typically much louder than the speaker's turbulence component, and because its energy is concentrated in the fundamental frequency F0 and harmonics thereof, the V stream is dominated by the EL components. This holds whether or not small amounts of turbulent sounds occur at the same frequency as in the superior in the V stream.

In a second aspect, the invention characterizes any short segment, i.e., the first list of 500–1000 samples as selected in step 120, as either an inter-word segment or not. This is possible using either the original input signal I values or the V values over the segment. This characterization for each segment may depend upon the total power in the segment, the presence of broad spectral peaks, in especially the V stream, or the characterization of preceding segments. We have found that total power alone is by far the simplest and adequately discriminating in many cases.

Figure 5:
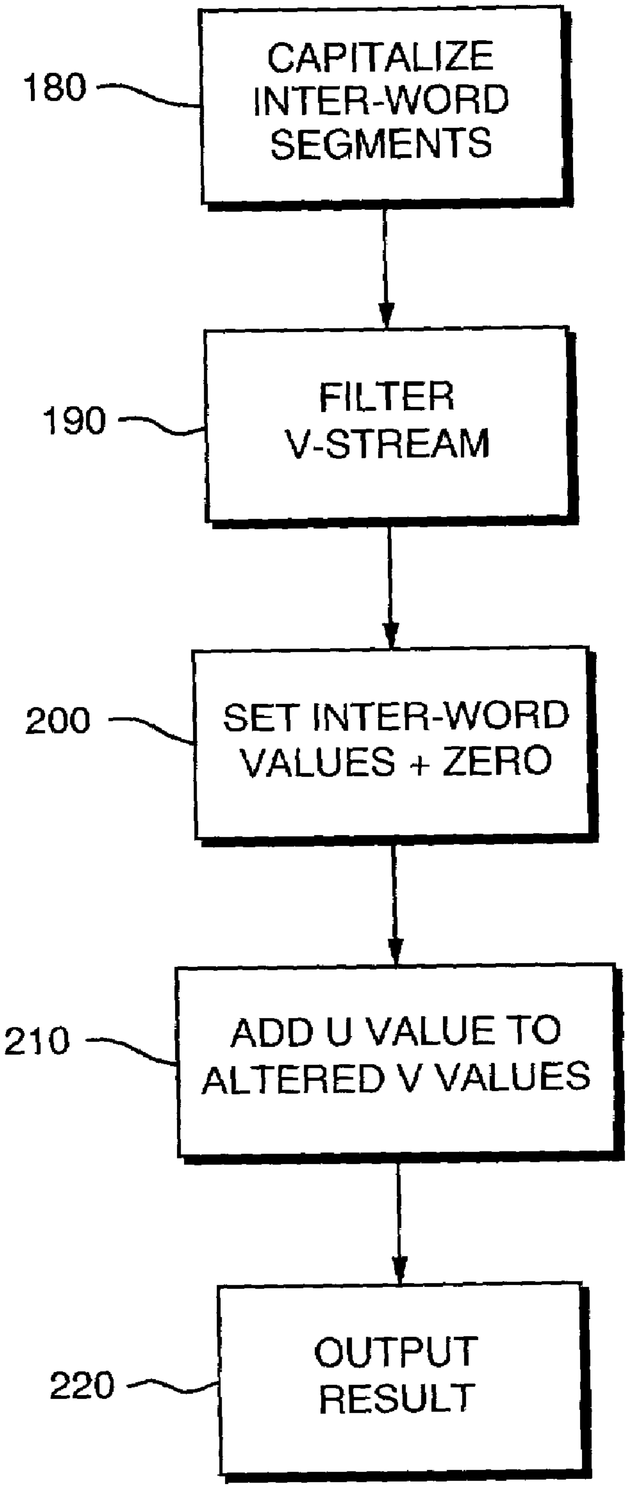
FIG. 5 is a sequence of steps performed to produce the resulting processed acoustic stream.

Such characterization may be performed in a further step 180 as shown in FIG. 5.

Following that, the algorithm may finish with the following steps.

First, the V stream is filtered in step 190 to improve its spectrum. The filter, for example, may be a linear filter that boosts low frequency energy and/or reduces high frequency energy.

In a next step 200, if the segment is determined to be an inter-word segment then its V values are set to 0.

Proceeding then to step 210, the U values are added, sample by sample, to the V values that were altered in step 200.

Finally, in step 220, the result may be output through digital analog converter, to produce the processed acoustic stream.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for processing an acoustic signal to separate the acoustic signal into a voiced (V) component corresponding to an electrolaryngeal source and an unvoiced (U) component corresponding to a turbulence source, the method comprising the steps of:

digitizing the acoustic signal to produce an original stream of numerical values;

extracting a segment of consecutive values from the original stream of numerical values to produce a first group of values covering two or more periods of the electrolaryngeal source;

performing a discrete Fourier transform on the first group of values to produce a discrete Fourier transform result;

extracting a second group of values from components of the discrete Fourier transform result which correspond to an electrolaryngeal fixed repetition rate, $F_0$, and harmonics thereof;

inverse-Fourier transforming the second group of values, to produce a representation of a segment of the V component;

concatenating multiple V component segments to form a V component sample stream;

determining the U component by subtracting the V component sample stream from the original stream of numerical values;

determining segments of the input acoustic signal that correspond to inter-word segments;

filtering the V component sample stream;

for segments determined to be inter-word segments, setting the corresponding values of the V component sample stream to a zero value;

adding the U component values to the altered V component sample stream values; and producing a processed acoustic sample stream from the addition of the U values and altered V values.

2. A method as in claim 1 wherein the step of determining inter-word segments includes a step of determining total power in the segments and characterizing such segments with relatively low power as inter-word segments.

3. A method as in claim 1 wherein the steps are performed in a digital signal processor connected in line with a telephone apparatus.

4. A method as in claim 1 wherein the step of determining inter-word segments further comprises:

determining an average power level for the group of values; and if the average power level of the group of values is below a threshold value, determining that the group of values corresponds to an inter-word segment of the acoustic signal.

5. A method as in claim 4 additionally comprising the step of:

if the average power level of the group of values is above a threshold value, determining that the group of values corresponds to a non-inter-word segment of the acoustic signal.

6. A method for processing an acoustic signal to separate the acoustic signal into a voiced (V) component corresponding to an electrolaryngeal source and an unvoiced (U) component corresponding to a turbulence source, the method comprising the steps of:

digitizing the acoustic signal to produce an original stream of numerical values;

extracting a segment of consecutive values from the original stream of numerical values to produce a first group of values covering two or more periods of the electrolaryngeal source;

performing a discrete Fourier transform on the first group of values to produce a discrete Fourier transform result;

extracting a second group of values from components of the discrete Fourier transform result which correspond to an electrolaryngeal fixed repetition rate, $F_0$, and harmonics thereof;

inverse-Fourier transforming the second group of values, to produce a representation of a segment of the V component;

concatenating multiple V component segments to form a V component sample stream;

determining the U component by subtracting the V component sample stream from the original stream of numerical values;

filtering the V component sample stream;

setting corresponding selected values of the V component sample stream to a zero value;

adding the U component values to the altered V component sample stream values; and producing a processed acoustic sample stream from the addition of the U values and altered V values.

7. A method as in claim 6 additionally comprising the step of:

setting the group of values to a zero value if they correspond to an inter-word segment.

* * * * *